United States Patent
Schmidt et al.

(10) Patent No.: US 7,081,241 B1
(45) Date of Patent: Jul. 25, 2006

(54) EXTRACELLULAR RAGE BINDING PROTEIN (EN-RAGE) AND USES THEREOF

(75) Inventors: Ann Marie Schmidt, Franklin Lakes, NJ (US); David Stern, Great Neck, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/167,705

(22) Filed: Oct. 6, 1998

(51) Int. Cl.
*A61K 39/395* (2006.01)

(52) U.S. Cl. ............... 424/130.1; 424/141.1; 424/142.1; 424/143.1; 514/2; 514/12

(58) Field of Classification Search ............ 514/2, 514/8, 12, 824, 885, 921; 424/130.1, 139.1, 424/143.1
See application file for complete search history.

(56) References Cited

U.S. PATENT DOCUMENTS 5,864,018 A * 1/1999 Morser et al. ........... 530/387.1

FOREIGN PATENT DOCUMENTS

| EP | 0731166 A | 9/1996 |
| WO | WO9739121 | 10/1997 |
| WO | WO9739125 | 10/1997 |

OTHER PUBLICATIONS

Hori et al, Journal of Biological Chemistry, vol. 27, No. 43, pp. 25752-25761, Oct. 1995.*
Ritthaler et al, American Journal of Pathology, vol. 146, No. 3, pp. 688-694, Oct. 1995.*
Voet et al. Biochemistry. 1990. John Wiley & Sons, Inc. 126-128 and 228-234.*
Mickle JE et al. Genotype-phenotype relationships in cystic fibrosis. Med Clin North Am. May 2000;84(3):597-607.*
Yan et al., Two-amino acid molecular switch in an epithelial morphogen that regulates binding to two distinct receptors. Science 290: 523-527, 2000.*
Baynes, J. W. (1991). Role of oxidative stress in development of complications in diabetes. *Diabetes* 40: 405-412 (Exhibit 2).

Borchelt, D. R., et al. (1996). Familial Alzheimer's Disease-linked presenilin 1 variants elevate $A\beta1-42/1-40$ ration *in vitro* and *in vivo*. *Neuron* 17: 1005-1013 (Exhibit 3).
Brett, J., et al. (1993). Survey of the distribution of a newly characterized receptor for a advanced glycation end products in tissues. *Am. J. Pathol.* 143(6): 1699-1712 (Exhibit 4).
Brownlee, M. (1992). Glycation products and the pathogenesis of diabetic complications. *Diabetes Care* 15(12): 1835-1842 (Exhibit 5).
Cai, X-D., et al. (1993). Release of excess amyloid $\beta$ protein from a mutant amyloid $\beta$ protein precursor. *Science* 259: 514-516 (Exhibit 6).
Citron, M., et al. (1997). Mutant presenilins of Alzheimer's Disease increase production of 42-residue amyloid $\beta$-protein in both transfected cells and transgenic mice. *Nature Medicine* 3(1): 67-72 (Exhibit 7).
Dell'Angelica, E. C., et al. (1994). Primary structure and binding properties of calgranulin C, a novel S100-like calcium-binding protein from pig granulocytes. *J. Biol. Chem.* 269: 28929-28936 (Exhibit 8).

(Continued)

*Primary Examiner*—Joseph Murphy
*Assistant Examiner*—Gregory S. Emch
(74) *Attorney, Agent, or Firm*—John P. White, Esq.; Cooper & Dunham LLP

(57) ABSTRACT

The present invention provides for an isolated human EN-RAGE peptide. The present invention also provides for a method for determining whether a compound is capable of inhibiting the interaction of an EN-RAGE peptide with a RAGE peptide, which comprises: (a) admixing: (i) a RAGE peptide or an sRAGE peptide or a fragment of either thereof, (ii) an EN-RAGE peptide or a fragment thereof, and (iii) the compound; (b) measuring the level of interaction between the peptide of step (a)(i) and the peptide of step (a)(ii), and (c) comparing the amount of interaction meaursed in step (b) with the amount measured between the peptide of step (a) (i) and the peptide of step (a) (ii) in the absence of the compound, thereby determining whether the compound is capable of inhibiting the interaction of the EN-RAGE peptide with the RAGE peptide, wherein a reduction in the amount of interaction in the presence of the compound indicates that the compound is capable of inhibiting the interaction. The present invention also provides for a method for inhibiting inflammation in a subject which comprises administering to the subject a compound capable of interfering with the interaction between EN-RAGE peptide and receptor for advanced glycation endproduct (RAGE) in the subject thereby inhibiting inflammation in the subject.

20 Claims, 5 Drawing Sheets

OTHER PUBLICATIONS

Fahey, T., et al. (1991). Diabetes impairs the late inflammatory response to wound healing. *J. Surg. Res.* 50: 308-313 (Exhibit 9).

Fu, M-X., et al. (1996). The advanced glycation end product, $N^\in$-(carboxymethly) lysine, is a product of both lipid peroxidation and glycoxidation reactions. *J. Biol. Chem.* 271: 9982-9986.

Giardino, I., et al. (1994). Nonenzymatic glycosylation *in vitro* and in bovine endothelial cells alters basic fibroblast growth factor activity. *J. Clin. Invest.* 94: 110-117 (Exhibit 11).

Gibbons, G. H. and V. J. Dzau. (1996). Molecular therapies for vascular diseases. *Science* 272: 689-693. (Exhibit 12).

Khoury, J. E., et al. (1994). Macrophages adhere to glucose-modified basement membrane collagen IV via their scavenger receptors. *J. Biol. Chem.* 269: 10197-10200 (Exhibit 13).

Kuo, Y-M., et al. (1996). Water-soluble Aβ (N-40, N-42) oligomers in normal and Alzheimer Disease brains. *J. Biol. Chem.* 271(8): 4077-4081 (Exhibit 14).

Lander, H. M., et al. (1997). Activation of the receptor for advanced glycation end products triggers a $p21^{ras}$ dependent mitogen-activated protein kinase pathway regulated by oxidant stress. *J. Biol. Chem.* 272: 17810-17814 (Exhibit 15).

Ledesma, M. D., et al. (1994). Analysis of microtubule-associated protein tau glycation in paired helical filaments. *J. Biol. Chem.* 269(34): 21614-21619 (Exhibit 16).

Li, J. and A. M. Schmidt (1997). Characterization and functional analysis of the promoter of RAGE, the receptor for advanced glycation end products. *J. Biol. Chem.* 272: 16498-16506 (Exhibit 17).

Lorenzo, A. and B. A. Yanker (1994). β-amyloid neurotoxicity requires fibril formation and is inhibited by Congo red. *Proc. Nat. Acad. Sci. USA* 91: 12243-12247 (Exhibit 18).

Mattson, M. P. and Y. Goodman (1995). Different amyloidogenic peptides share a similar mechanism of neurotoxicity involving reactive oxygen species and calcium. *Brain Res.* 676: 219-224 (Exhibit 19).

Miyata, T., et al. (1996). The receptor for advanced glycation end products (RAGE) is a central mediator of the interaction of AGE-β2 Microglobulin with human mononuclear phagocytes via an oxidant-sensitive pathway. *J. Clin. Invest.* 98: 1088-1094 (Exhibit 20).

Nakamura, Y., et al. (1993). Immunohistochemical localization of advanced glycosylation endproducts in coronary atheroma and cardiac tissue in diabetes mellitus. *Am. J. Pathol.* 143(6): 1649-1656 (Exhibit 21).

Neeper, M., et al. (1992). Cloning and expression of a cell surface receptor for advanced glycosylation end products of proteins. *J. Biol. Chem.* 267: 14998-15004 (Exhibit 22).

Palinski, W., et al. (1995). Immunological evidence for the presence of advanced glycosylation end products in atherosclerotic lesions of euglycemic rabbits. *Arterioscl. Thromb. and Vasc. Biol.* 15(5): 571-582 (Exhibit 23).

Park, L., et al. (1998). Suppression of accelerated diabetic atherosclerosis by the soluble receptor for advanced glycation endproducts. *Nature Medicine* 4: 1025-1031 (Exhibit 24).

Park, L., et al. (1997). A murine model of accelerated diabetic atherosclerosis: suppression by soluble receptor for advanced glycation endproducts. *Circulation Supplement.* Abstract 3079 (Exhibit 25).

Reddy, S., et al. (1995). $N^\in$-(Carboxymethyl) lysine is a dominant advanced glycation end product (AGE) antigen in tissue proteins. *Biochemistry* 34: 10872-10878 (Exhibit 26).

Renard, C., et al. (1997). Recombinant advanced glycation end product receptor pharmacokinetics in normal and diabetic rats. Mol. Pharm. 52: 54-62 (Exhibit 27).

Roher, A. E., et al. (1996). Morphology and toxicity of Aβ-(1-42) dimer derived from neuritic and vascular amyloid deposits of Alzheimer's Disease. *J. Biol. Chem.* 271(34): 20631-20635 (Exhibit 28).

Schleicher, E. D., et al. (1997). Increased accumulation of the glycoxidation product $N^\in$-(carboxymethyl) lysine in human tissues in diabetes and aging. *J. Clin. Invest.* 99: 457-468 (Exhibit 29).

Schmidt, A. M., et al. (1995). Advanced glycation endproducts interacting with their endothelial receptor induce expression of vascular cell adhesion molecule-1 (VCAM-1) in cultured human endothelial cells and in mice. *J. Clin Invest.* 96: 1395-1403 (Exhibit 30).

Schmidt, A. M., et al. (1994). Receptor for advanced glycation endproducts (AGEs) has a central role in vessel wall interactions and gene activation in response to circulating AGE proteins. *Proc. Nat'l Acad. Sci. USA* 91: 8807-8811 (Exhibit 31).

Schmidt, A. M., et al. (1992). Isolation and characterization of two binding proteins for advanced glycosylation end products from bovine lung which are present on the endothelial cell surface. *J. Biol. Chem.* 267: 14987-14997 (Exhibit 32).

Schmidt, A. M., et al. (1994). Cellular receptors for advanced glycation end products. *Arterioscler. Thromb.* 14: 1521-1528 (Exhibit 33).

Schmidt, A. M., et al. (1995). The dark side of glucose. (News and Views). *Nature Medicine* 1: 1002-1004 (Exhibit 34).

Schmidt, A. M., et al. (1993). Regulation of human mononuclear phagocyte migration by cell surface-binding proteins for advanced glycation end products. *J. Clin. Invest.* 92: 2155-2168 (Exhibit 35).

Schmidt, A. M., et al. (1997). The v-domain of receptor for advanced glycation endproducts (RAGE) mediates binding of AGEs: a novel target for therapy of diabetic complications. *Circulation Supplement* 96:#194, p. 1-37 (Exhibit 36).

Schmidt, A. M., et al. (1994). The endothelial cell binding site for advanced glycation end products consists of a complex: an integral membrane protein and a lactoferrin-like polypeptide. *J. Biol. Chem.* 269: 9882-9888 (Exhibit 37).

Soulis, T., et al. (1997). Advanced glycation end products and their receptors co-localise in rat organs susceptible to diabetic microvascular injury. *Diabetologia* 40: 619-628 (Exhibit 38).

Turner, R. S., et al. (1997). Amyloids $β_{40}$ and $β_{42}$ are generated intracellularly in cultured human neurons and their secretion increases with maturation. *J. Biol. Chem.* 271 (15): 8966-8970 (Exhibit 39).

Vitek, M. P., et al. (1994). Advanced glycation end products contribute to amyloidosis in Alzheimer disease. *Proc. Nat'l Acad. Sci. USA* 91: 4766-4770 (Exhibit 40).

Vlassara, H., et al. (1995). Identification of galectin-3 as a high-affinity binding protein for advanced glycation end products (AGE): a new member of the AGE-receptor complex. *Molec. Med.* 1: 634-646 (Exhibit 41).

Vlassara, H., et al. (1994). Pathogenic effects of advanced glycosylation: biochemical, biologic, and clinical implications for diabetes and aging. *Lab. Invest.* 70: 138-151 (Exhibit 42).

Wautier, J.-L., et al. (1996). Receptor-mediated endothelial cell dysfunction in diabetic vasculopathy: soluble receptor for advanced glycation end products blocks hyperpermeability in diabetic rats. *J. Clin. Invest.* 97: 238-243 (Exhibit 43).

Wautier, J.-L., et al. (1996). Interaction of diabetic erythrocytes bearing advanced glycation endproducts with the endothelial receptor AGE induces generation of reactive oxygen intermediates and cellular dysfunction. *Circulation Supplement* 94(8): #4139 (Exhibit 44).

Wu J., et al. (1997). The soluble receptor for advanced glycation endproducts (sRAGE) ameliorates impaired wound healing in diabetic mice. *Plastic Surg. Res. Council* Abstract #77, p. 43 (Exhibit 45).

Yan, S. D., et al. (1994). Enhanced cellular oxidant stress by the interaction of advanced glycation end products with their receptors/binding proteins. *J. Biol. Chem.* 269: 9889-9897 (Exhibit 46).

Yan, S. D., et al. (1996). RAGE and amyloid-$\beta$ peptide neurotoxicity in Alzheimer's disease. *Nature* 382: 685-691 (Exhibit 47); and.

Yan, S. D., et al. (1997). Amyloid-$\beta$ peptide-receptor for advanced glycation endproduct interaction elicits neuronal expression of macrophage-colony stimulating factor: a proinflammatory pathway in Alzheimer disease. *Proc. Nat'l Acad. Sci.* 94: 5296-5301. (Exhibit 48).

Dec. 22, 2005 Communication from the European Patent Office transmitting a Supplementary Partial European Search Report Under Rule 46(1) EPC in connection with European Patent Application No. 99953081.9, filed Oct. 6, 1999.

Database EMBL "*Homo Sapiens* RAGE binding protein mRNA, complete cds," retrieved from EMB Accession No. EM_PRO: AF011757 (1998).

Mar. 24, 2005 Communication from the European Patent Office transmitting a Supplementary Partial European Search Report Under Rule 45 EPC in connection with European Patent Application No. 99953081.9, filed Oct. 6, 1999.

Miyata, T., et al., "The receptor for advanced glycation end products (RAGE) is a central mediator of the interaction of AGE-$\beta_2$ microglobulin with human mononuclear phagocytes via an oxidant-sensitive pathway: Implications for the pathogenesis of dialysis-related amyloidosis," Journal of Clinical Investigation 98: 1088-1094 (1996).

Hori, O., et al., "The receptor for advanced glycation end-products has a central role in mediating the effects of advanced glycation end-products of the development of vascular disease in diabetes mellitus," Nephrology Dialysis Transplantation 11: 13-16 (1996).

Li, J., et al., "Characterization and functional analysis of the promoter of RAGE, the receptor for advanced glycation end products," Journal of Biological Chemistry 272: 16498-16506 (1997).

Hofman, M., et al., "EN-RAGE (extracellular novel-RAGE binding protein) activates endothelial cells and macrophages to mediate inflammatory responses," Circulation 98: I316 (1998).

* cited by examiner

*FIGURE 5*

ATGACTAAGCTGGAGGACCACCTGGAGGAATCATCAACATCTTC
CACCAGTACTCCGTTCGGGTGGGCATTTCGACACCCTCAACAAG
CGTGAGCTGAAGCAGCTGATCACAAGGAACTTCCCAAAACCCT
CCAGAAACACCAAAGACCAACCTACCATTGACAAATATTCCAAGA
CCTGGATGCCGATAAAGACGGGAGCCGTCAGCTTTGAGGAATTCGT
AGTCCTGGTGTCCAGGGTGCTGAAAACAGCCCACATAGATATCCA
CAAAGAGTAGGTTTCCAGCAATGTTCCAAGAAGACTTACCCTTCT
CCTCCCTGAGGCTGCTCCCGAGGGAGAGAGAATTATAAACGTAC
TTTGGCAAATTCTTAGCAAAAAAAAAAAAAAA

SEQUENCE LISTING

<160> NUMBER OF SEQ ID NOS: 5

<210> SEQ ID NO 1
<211> LENGTH: 395
<212> TYPE: DNA
<213> ORGANISM: Bovine

<400> SEQUENCE: 1

```
atgactaagc tggaggacca cctggaggga atcatcaaca tcttccacca gtactccgtt    60
```

-continued

```
cgggtggggc atttcgacac cctcaacaag cgtgagctga agcagctgat cacaaaggga    120
acttcccaaa accctccaga acaccaaaga ccaacctacc attgacaaaa tattccaaga    180
cctggatgcc gataaagacg gagccgtcag ctttgaggaa ttcgtagtcc tggtgtccag    240
ggtgctgaaa acagcccaca tagatatcca caaagagtag gtttccagca atgttcccaa    300
gaagacttac ccttctcctc cctgaggctg ctccccgagg gagagagaat tataaacgta    360
ctttggcaaa ttcttagcaa aaaaaaaaaa aaaaa                                395
```

<210> SEQ ID NO 2
<211> LENGTH: 50
<212> TYPE: PRT
<213> ORGANISM: Human
<220> FEATURE:
<221> NAME/KEY: UNSURE
<222> LOCATION: (47)
<223> OTHER INFORMATION: Xaa at this position is unknown

<400> SEQUENCE: 2

```
Thr Lys Leu Glu Asp His Leu Glu Gly Ile Ile Asn Ile Gly His Gln
 1               5                  10                  15

Tyr Ser Val Arg Val Gly His Phe Asp Thr Leu Asn Lys Tyr Glu Leu
            20                  25                  30

Lys Gln Leu Gly Thr Lys Glu Leu Pro Lys Thr Leu Gln Asn Xaa Lys
        35                  40                  45

Asp Gln
    50
```

<210> SEQ ID NO 3
<211> LENGTH: 90
<212> TYPE: PRT
<213> ORGANISM: Human

<400> SEQUENCE: 3

```
Thr Lys Leu Glu Asp His Leu Glu Gly Ile Ile Asn Ile Phe His Gln
 1               5                  10                  15

Tyr Ser Val Arg Val Gly His Phe Asp Thr Leu Asn Lys Arg Glu Leu
            20                  25                  30

Lys Gln Leu Ile Thr Lys Glu Leu Pro Lys Thr Leu Gln Asn Thr Lys
        35                  40                  45

Asp Gln Pro Thr Ile Asp Lys Ile Phe Gln Asp Leu Asp Ala Asp Lys
50                  55                  60

Asp Gly Ala Val Ser Phe Glu Glu Phe Val Val Leu Val Ser Arg Val
65                  70                  75                  80

Leu Lys Thr Ala His Ile Asp Ile His Lys
            85                  90
```

<210> SEQ ID NO 4
<211> LENGTH: 18
<212> TYPE: PRT
<213> ORGANISM: Human

<400> SEQUENCE: 4

```
Asp Gly Ala Val Ser Phe Glu Glu Phe Val Val Leu Val Ser Arg Val
 1               5                  10                  15

Leu Lys
```

<210> SEQ ID NO 5
<211> LENGTH: 5
<212> TYPE: PRT

```
<213> ORGANISM: Human

<400> SEQUENCE: 5

Ala Gln Asn Ile Thr
 1               5
```

US 7,081,241 B1

EXTRACELLULAR RAGE BINDING PROTEIN (EN-RAGE) AND USES THEREOF

The invention disclosed herein was made with Government support under NIH Grant No. AG00602 from the U.S. Department of Health and Human Services. Accordingly, the U.S. Government has certain rights in this invention.

BACKGROUND OF THE INVENTION

Throughout this application, various publications are referenced by author and date within the text. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

The Receptor for AGE (RAGE) is a member of the immunoglobulin superfamily of cell-surface molecules (1–2). Originally identified and characterized as a cellular receptor for glucose (aldose sugar)-modified proteins, or Advanced Glycation Endproducts (AGEs) (3–13), RAGE has subsequently been reported to interact with other ligands, in both settings of normal development and in Alzheimer's disease (14–16). In normal development, RAGE interacts with amphoterin, a polypeptide which mediates neurite outgrowth in cultured embryonic neurons. In those studies, either anti-RAGE F(ab')$_2$ or soluble RAGE (sRAGE) inhibited neurite outgrowth on amphoterin-coated matrices, but not on matrices coated with other substrates such as laminin or poly-l-lysine (3). In later studies, RAGE was identified as a receptor on neurons and microglia for amyloid-β-peptide, a polypeptide linked to the pathogenesis of neuronal toxicity and death in Alzheimer's disease.

SUMMARY OF THE INVENTION

The present invention provides for an isolated human EN-RAGE peptide. The present invention also provides for a method for determining whether a compound is capable of inhibiting the interaction of an EN-RAGE peptide with a RAGE peptide, which comprises: (a) admixing: (i) a RAGE peptide or an sRAGE peptide or a fragment of either thereof, (ii) an EN-RAGE peptide or a fragment thereof, and (iii) the compound; (b) measuring the level of interaction between the peptide of step (a) (i) and the peptide of step (a) (ii), and (c) comparing the amount of interaction meausred in step (b) with the amount measured between the petpide of step (a) (i) and the peptide of step (a) (ii) in the absence of the compound, thereby determining whether the compound is capable of inhibiting the interaction of the EN-RAGE peptide with the RAGE peptide, wherein a reduction in the amount of interaction in the presence of the compound indicates that the compound is capable of inhibiting the interaction. The present invention also provides for a method for inhibiting inflammation in a subject which comprises administering to the subject a compound capable of interfering with the interaction between EN-RAGE peptide and receptor for advanced glycation endproduct (RAGE) in the subject thereby inhibiting inflammation in the subject.

BRIEF DESCRIPTION OF THE FIGURES

FIG. 5. Nucleic Acid Sequence of bovine EN-RAGE. The cDNA for bovine EN-RAGE was cloned and deposited with Genbank at Accession No. AF 011757. The sequence (5' to 3') is shown in FIG. 5 (SEQ ID NO. 1).

DETAILED DESCRIPTION OF THE INVENTION

Figure 1:
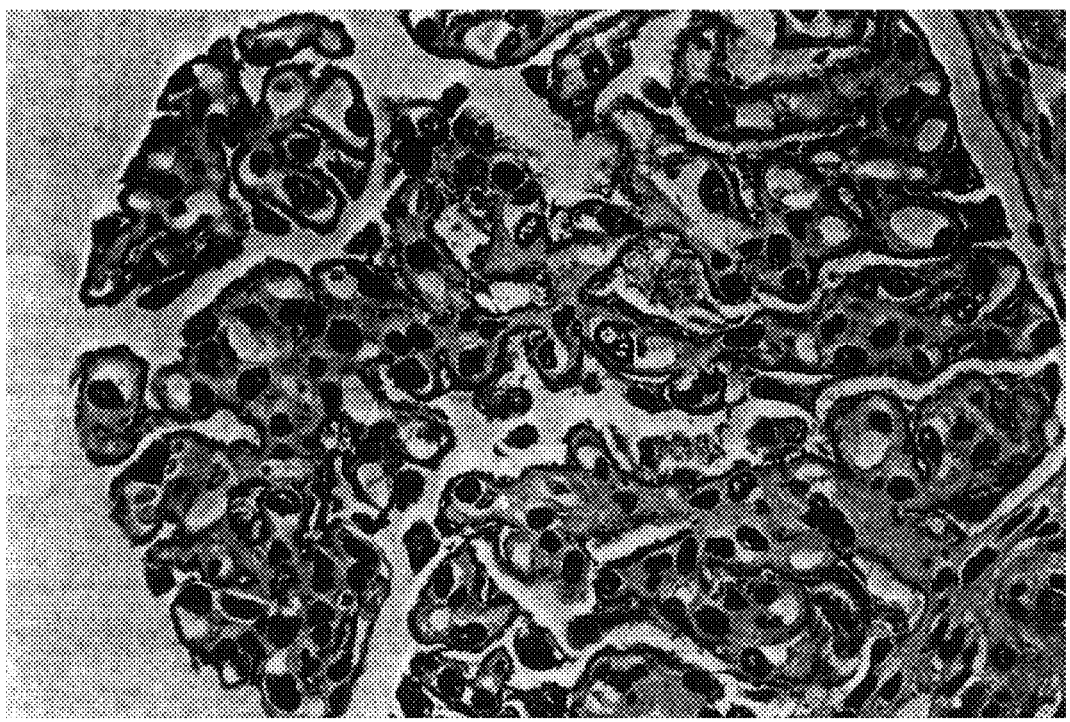
FIG. 1. Immunohistochemistry of human kidney (active lupus nephritis). Kidney tissue from a patient with active lupus nephritis was obtained, fixed in formalin and paraffin-embedded sections were prepared. Sections were stained with rabbit anti-RAGE IgG. Increased expression of RAGE was noted in the podocytes of the glomerulus.

The following abbreviations are used herein: CML—carboxymethyl-lysine; AGE—advanced glycation endproduct(s); RAGE—receptor for advanced glycation endprocut(s); sRAGE—soluble receptor for advanced glycation endproduct(s); EN-RAGE—Extracellular Novel RAGE Binding Protein.

The present invention provides for an isolated human EN-RAGE peptide. In one embodiment, the isolated EN-RAGE peptide having the N-terminal amino acid sequence shown in Table 1. In another embodiment, the EN-RAGE peptide is encoded by the cDNA sequence of Genbank Accession No. AF 011 757. An isolated nucleic acid molecule encoding an EN-RAGE peptide. In one embodiment, the EN-RAGE peptide is human EN-RAGE. In another embodiment, the nucleic acid is DNA, cDNA or RNA. In one example, the nucleic acid sequence of the EN-RAGE is the sequence shown in FIG. 5 (Seq I.D. No. 1).

The present invention also provides for a replicable vector comprising the EN-RAGE nucleic acid molecule. In one embodiment, the replicable vector is a prokaryotic expression vector, a yeast expression vector, a baculovirus expression vector, or a mammalian expression vector.

The present invention also provides for a host cell comprising the replicable vector. In one embodiment, the host cell is a eukaryotic cell, a somatic cell, or a germ cell.

In another embodiment, the nucleic acid molecule of the invention may be labelled with a detectable moiety. The detectable moiety may be selected from the group consisting of: a fluorescent label, a digoxigenin, a biotin, an enzyme, a radioactive atom, a paramagnetic ion, and a chemiluminescent label.

The present invention also provides for nucleic acid molecule consisting essentially of a unique fragment of an EN-RAGE nucleic acid sequence in a 3' to 5' orientation, wherein the sequence antisense to at least a portion of a gene encoding naturally occurring EN-RAGE peptide.

The present invention also provides a composition comprising an EN-RAGE peptide or fragment thereof and a pharmaceutically acceptable carrier. In one embodiment, the pharmaceutically acceptable carrier is an aerosol, intravenous, oral or topical carrier.

The present invention also provides for an antibody immunoreactive with an epitope comprising a unique sequence of EN-RAGE.

The present invention also provides for a ribozyme which is capable of specifically cleaving EN-RAGE mRNA in a cell.

The present invention also provides for a transgenic nonhuman mammal whose germ or somatic cells contain a nucleic acid molecule which encodes an EN-RAGE peptide or a biologically active variant thereof, introduced into the mammal, or an ancestor thereof, at an embryonic stage. In one embodiment, the nucleic acid molecule which encodes EN-RAGE polypeptide is overexpressed in the cells of the mammal. In another embodiment, the nucleic acid molecule encodes human EN-RAGE peptide. In another embodiment, the active variant comprises a homolog of EN-RAGE.

The present invention also provides for a transgenic nonhuman mammal whose germ or somatic cells have been transfected with a suitable vector with an appropriate sequence designed to reduce expression levels of EN-RAGE peptide below the expression levels of that of a native mammal. In one embodiment, the suitable vector contains an appropriate piece of cloned genomic nucleic acid sequence to allow for homologous recombination. In another emboidment, the suitable vector encodes a ribozyme capable of cleaving an EN-RAGE mRNA molecule or an antisense molecule which comprises a sequence antisense to naturally occurring EN-RAGE mRNA sequence.

The present invention also provides for a method for determining whether a compound is capable of inhibiting the interaction of an EN-RAGE peptide with a RAGE peptide, which comprises: (a) admixing: (i) a RAGE peptide or an sRAGE peptide or a fragment of either thereof, (ii) an EN-RAGE peptide or a fragment thereof, and (iii) the compound; (b) measuring the level of interaction between the peptide of step (a) (i) and the peptide of step (a) (ii), and (c) comparing the amount of interaction meausred in step (b) with the amount measured between the peptide of step (a) (i) and the peptide of step (a) (ii) in the absence of the compound, thereby determining whether the compound is capable of inhibiting the interaction of the EN-RAGE peptide with the RAGE peptide, wherein a reduction in the amount of interaction in the presence of the compound indicates that the compound is capable of inhibiting the interaction.

In one embodiment, the fragment of step (a) (i) is the V-domain of RAGE. In another embodiment, the fragment of step (a) (i) or (a)(ii) is synthetic. In another embodiment, the compound comprises at least a portion of naturally occuring sRAGE peptide. In another embodiment, the compound is a peptidomimetic. In another embodiment, the compound is an organic molecule. In another embodiment, the compound is a peptide, a nucleic acid or an inorganic chemical. In another embodiment, the compound is a molecule of less than 10,000 daltons. In another embodiment, the compound is an antibody or fragment thereof. In another embodiment, the compound is a mutated RAGE peptide or a fragment thereof. In another embodiment, the compound is a mutated sRAGE peptide or a fragment thereof. In another embodiment, the compound is a mutated EN-RAGE peptide or a fragment thereof. In another embodiment, the peptide of step (a) (i) is affixed to a solid surface. In another embodiment, the peptide of step (a)(ii) is affixed to a solid surface. In another embodiment, the peptide of step (a) (i) or (a) (ii) is detectably labeled. In another embodiment, the detectable label comprises fluorescence, biotin, or radioactivity.

In another embodiment, the admixing in the screening method occurs in a cell. In another embodiment, the admixing occurs in an animal.

The present invention also provides for a compound identified by the screening method described herein which compound is useful for the suppression of inflammation in a subject.

The present invention also provides for a compound identified by the method described herein which is useful for the treatment of systemic lupus erythematosus or inflammatory lupus nephritis in a subject.

The present invention provides for a previously unknown compound identified by the method described hereinabove.

The present invention also provides for a method for inhibiting inflammation in a subject which comprises administering to the subject a compound capable of interfering with the interaction between EN-RAGE peptide and receptor for advanced glycation endproduct (RAGE) in the subject thereby inhibiting inflammation in the subject.

In another embodiment, the compound is an anti-EN-RAGE antibody or a fragment thereof or an anti-RAGE antibody or fragment thereof. In another embodiment, the compound is an sRAGE peptide. In another embodiment, the compound consists essentially of the ligand binding domain of sRAGE peptide or the ligand binding domain of EN-RAGE peptide. In another embodiment, the compound is a nucleic acid molecule or a peptide. In another embodiment, the peptide is an antibody or a fragment thereof. In another embodiment, the nucleic acid molecule is a ribozyme or an antisense nucleic acid molecule. In another embodiment, the compound is a compound identified by the screening method described hereinabove.

In another embodiment, the inflammation is assoicated with delayed hypersensitivity, accelerated athrosclerosis, or lupus nephritis. In another embodiment, the subject is a human, a primate, a mouse, a rat or a dog.

In another embodiment, the administration comprises intralesional, intraperitoneal, intramuscular or intravenous injection; infusion; liposome-mediated delivery; or topical, intrathecal, gingival pocket, per rectum, intrabronchial, nasal, oral, ocular or otic delivery. In another embodiment, the compound is administered hourly, daily, weekly, monthly or annually. In another embodiment, the effective amount of the compound comprises from about 0.000001 mg/kg body weight to about 100 mg/kg body weight.

In another embodiment, the subject is suffering from systemic lapus erythematosus, inflammatory lupus nephritis, septic shock or endotoxemia. In another embodiment, the subject is suffering from inflammation.

In a further embodiment, the subject is suffering from an autoimmune or inflammatory disorder in which recruitment of EN-RAGE-containing inflammatory cells occurs. In another embodiment, the subject is suffering from a bacterial-associated or other pathogen-associated infection.

In another embodiment, the method further comprises administering to the subject a pharmaceutically acceptable carrier during the administration of the compound. In another embodiment the carrier comprises a diluent. In another embodiment, the carrier comprises, a virus, a liposome, a microencapsule, a polymer encapsulated cell or a retroviral vector. In another embodiment, the carrier is an aerosol, intravenous, oral or topical carrier. In another embodiment, the compound is administered from a time release implant.

The present invention also provides for a method for determining whether a compound is capable of inhibiting the ability of EN-RAGE protein to bind with a second protein which comprises: (a) admixing the EN-RAGE protein, the second protein and the compound; (b) measuring the amount of binding between the EN-RAGE protein and the second protein; and (c) comparing the amount of binding measured in step (b) with the amount of binding between EN-RAGE and the second protein in the absence of the compound, wherein a reduction in the amount of binding indicates that the compound is capable of inhibiting the ability of EN-RAGE protein to bind with the second protein.

Figure 3:
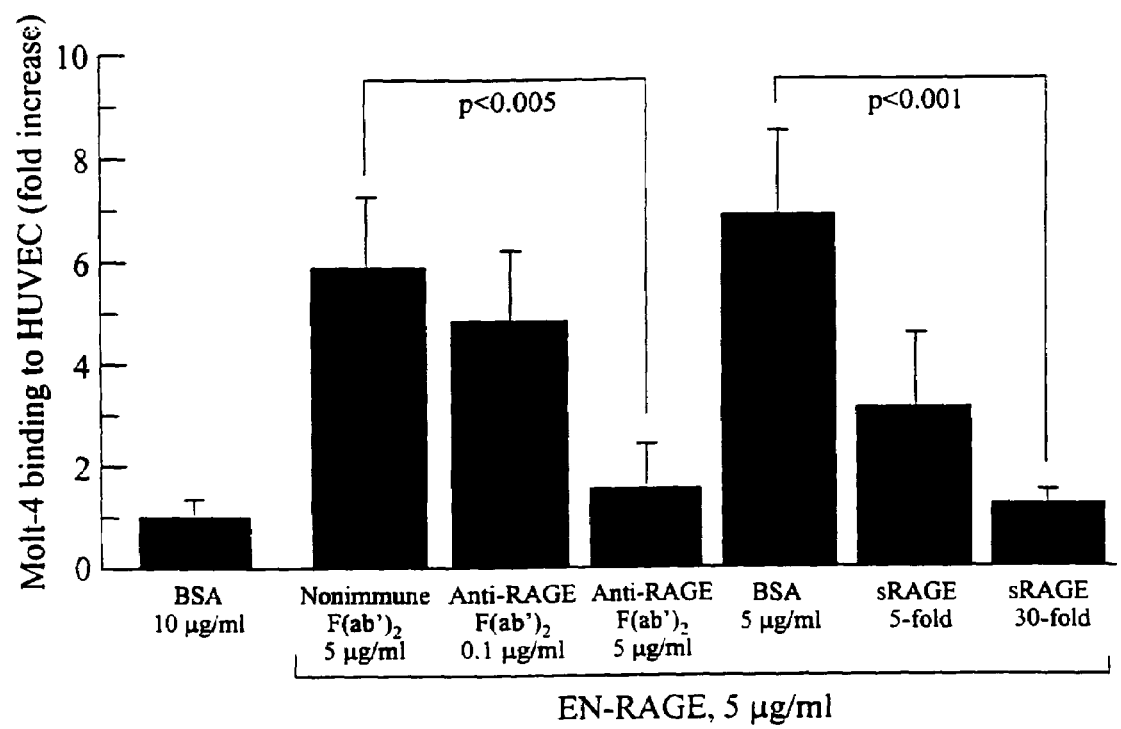
FIG. 3. Incubation of HUVECs with EN-RAGE increases VCAM-1 functional activity: increased binding of Molt-4 cells. Assessment of functional VCAM-1 activity was determined using $^{51}$Cr-labelled Molt-4 cells (ATCC) as described above. HUVEC were treated with either BSA (10 µg/ml) or EN-RAGE (5 µg/ml) for eight hrs. Molt-4 cells (5×10$^7$/ml) were incubated for 2 hrs in RPMI containing$^{51}$ Cr (0.1 mCi). At the end of that time, cells were washed with PBS and then added to the monolayer of treated HUVEC for one hour. Unbound Molt-4 cells were removed by washing three times with PBS. Cells were then lysed in buffer containing triton-X 100 (2%) in order to release Molt-4 cell-bearing radioactivity. Statistical considerations are shown in the figure.
Figure 4:
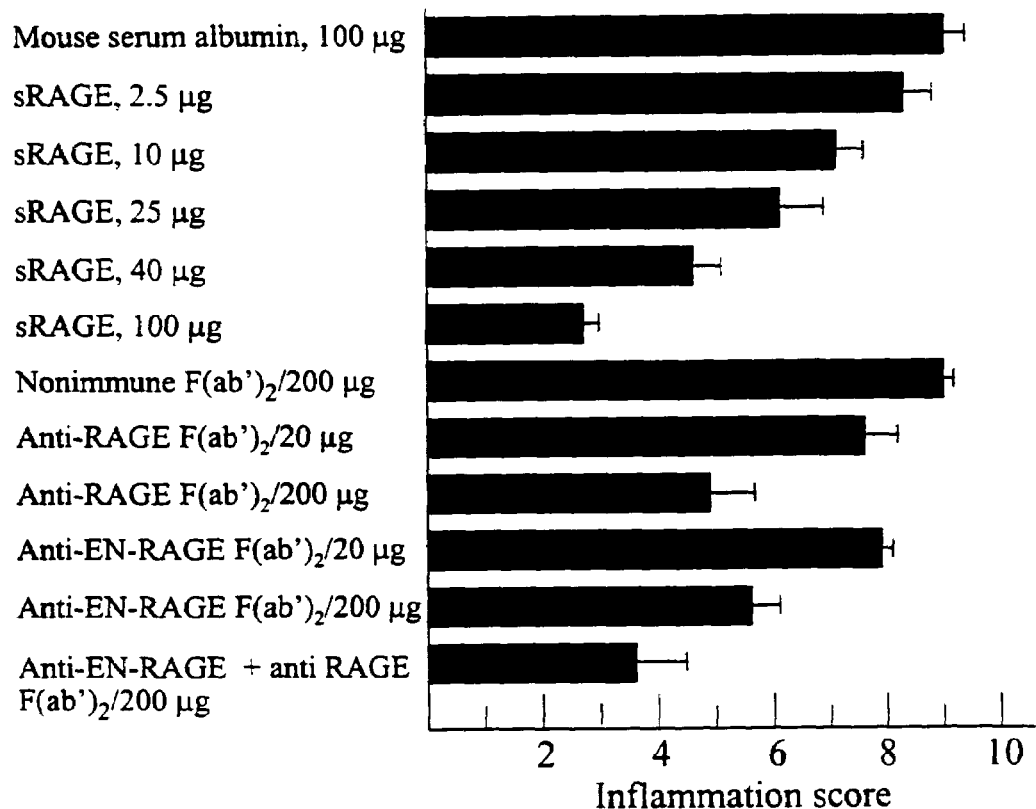
FIG. 4. Delayed hypersensitivity model: suppression of inflammation in the presence of soluble RAGE. CF-1 mice were sensitized with mBSA; after three weeks, mBSA was injected into the hind foot pad. Certain mice were treated with the indicated concentrations of mouse serum albumin, sRAGE or the indicated F(ab')$_2$ antibody fragments of RAGE or EN-RAGE. Inflammation score was defined as above (scale; 1–9).

The human cDNA of RAGE is 1406 base pairs and encodes a mature protein of 404 amino acids. See FIG. 3 of Neeper et al. 1992. As used herein, "V-domain of RAGE" refers to the immunoglobulin-like variable domain as shown in FIG. 5 of Neeper, M., Schmidt, A. M., Brett, J., Yan, S. D., Wang, F., Pan, Y. C., Elliston, K., Stern, D., and Shaw, A. Cloning and expression of RAGE: a cell surface receptor for advanced glycosylation end products of proteins. J. Biol. Chem. 267:14998–15004, 1992 the contents of which are hereby incorporated by reference. The V-domain includes amino acids from position 23 to position 120 as shown in FIG. 4 of Neeper et al. (1992). The leader sequence shown is not part of the V-domain and in the human, t domain begins with the amino acids A-Q-N-I-T(SEQ ID NO: 5) . . . . The minimum required amino acid sequence to define the AGE binding site in the RAGE protein may be much smaller than 120 amino acids.

The bovine EN-RAGE nucleic acid sequence has been cloned and has been deposited with Genbank at Accession No. AF 011757. The nucleic acid sequence of EN-RAGE is shown in FIG. 5. Homologs of EN-RAGE present in other species would be obtainable via methods known to one of skill in the art. For example, sequences unique to the bovine EN-RAGE nucleic acid cDNA sequence may be used as probes to screen a human cDNA library in order to obtain the human homolog.

Ligands for RAGE such as AGEs (CML-modified AGEs) and p12, a proinflammatory cytokine, activate inflammatory cells. This has been shown in mice. These activation effects are blocked in the presence of sRAGE. Thus, the present invention provides methods for blocking inflammation (e.g., inflammation due to immune stimulation) in a subject by administering a compound which is capable of interfering with the interaction between EN-RAGE and RAGE in a subject. Such a method would be selective for inflammation.

The compound, in one example, is designed specifically as a competitive inhibitor of ligands for RAGE.

The screening assay may be carried out wherein one of the components is bound or affixed to a solid surface. In one embodiment the peptide is affixed to a solid surface. In another embodiment, the second peptide which has the sequence of the AGE binding site of RAGE is bound or affixed to a solid surface. The solid surfaces useful in this embodiment would be known to one of skill in the art. For example, one embodiment of a solid surface is a bead, a column, a plastic dish, a plastic plate, a microscope slide, a nylon membrane, etc. The material of which the solid surface is comprised is synthetic in one example.

One of the components of step (a) of the screening assay may be detectably labelled. The component (either the compound, the peptide or the V-domain or second peptide) may be labeled with a detectable moiety including a fluorescent label, a biotin, a digoxigenin, a radioactive atom, a paramagnetic ion, and a chemiluminescent label. The component may be labeled by covalent means such as chemical, enzymatic or other appropriate means with a moiety such as an enzyme or radioisotope.

In one embodiment, the subject is be a mammal. In another embodiment, the subject is a vertebrate. In a preferred embodiment, the mammal is a human. In one example, the subject is a diabetic subject. In another example of the invention, the subject is suffering from diabetes, renal failure, amyloidoses, aging or inflammation. The subject may be an obese subject as defined by the American Medical Association height and weight standards. The subject may be aged. The subject may be a human, a primate, an equine subject, an opine subject, an avian subject, a bovine subject, a porcine, a canine, a feline or a murine subject.

In one embodiment, the subject is suffering from an AGE-related disease. In another embodiment, such AGE-related disease is manifest in the brain, retina, kidney, vasculature, heart, or lung. In another embodiment, the subject is suffering from Alzheimer's disease or a disease which is manifested by AGEs accumulating in the subject. In another embodiment, the subject is suffering from symptoms of diabetes such as soft tissue injury, reduced ability to see, cardiovascular disease, kidney disease, etc. Such symptoms would be known to one of skill in the art.

The compound may be a polypeptide. The polypeptide may be a peptide; a peptidomimetic, a synthetic polypeptide, a derivative of a natural polypeptide, a modified polypeptide, a labelled polypeptide, or a polypeptide which includes non-natural peptides. The peptidomimetic may be identified from screening large libraries of different compounds which are peptidomimetics to determine a compound which is capable of preventing accelerated atherosclerosis in a subject predisposed thereto. The polypeptide may be a non-natural polypeptide which has chirality not found in nature, i.e. D-amino acids or L-amino acids.

In one embodiment, the compound is an antagonist, wherein the antagonist is capable of binding the RAGE with higher affinity than AGEs, thus competing away the effects of AGE's binding.

In another embodiment, the compound may be a ribozyme which is capable of inhibiting expression of RAGE. In another embodiment, the compound is an anti-RAGE antibody, an anti-AGE antibody, an anti-V-domain of RAGE antibody. The antibody may be monoclonal, polyclonal, chimeric, humanized, primatized. The compound may be a fragment of such antibody.

In another embodiment of the present invention, the method may further comprise administering to the subject a pharmaceutically acceptable carrier during the administration of the polypeptide. The administration may comprise intralesional, intraperitoneal, intramuscular or intravenous injection; infusion; liposome-mediated delivery; or topical, nasal, oral, ocular or otic delivery. In a further embodiment, the administration includes intrabronchial administration, anal or intrathecal administration.

The polypeptide may be delivered hourly, daily, weekly, monthly, yearly (e.g. in a time release form) or as a one time delivery. The delivery may be continuous delivery for a period of time, e.g. intravenous delivery.

The effective amount of the polypeptide may comprise from about 0.000001 mg/kg body weight to about 100 mg/kg body weight. In one embodiment, the effective amount may comprise from about 0.001 mg/kg body weight to about 50 mg/kg body weight. In another embodiment, the effective amount may range from about 0.01 mg/kg body weight to about 10 mg/kg body weight. The actual effective amount will be based upon the size of the polypeptide, the biodegradability of the polypeptide, the bioactivity of the polypeptide and the bioavailability of the polypeptide. If the polypeptide does not degrade quickly, is bioavailable and highly active, a smaller amount will be required to be effective. The effective amount will be known to one of skill in the art; it will also be dependent upon the form of the polypeptide, the size of the polypeptide and the bioactivity of the polypeptide. One of skill in the art could routinely perform empirical activity tests for a polypeptide to determine the bioactivity in bioassays and thus determine the effective amount.

In another embodiment of the present invention, the method may further comprise administering a pharmaceutically acceptable carrier to the subject during the administration of the compound. The administration may comprise intralesional, intraperitoneal, intramuscular or intravenous injection; infusion; liposome-mediated delivery; or topical, nasal, oral, ocular or otic delivery.

The compound may be administered hourly, daily, weekly, monthly, yearly (e.g. in a time release form) or as a one time delivery. The delivery or administration may be continuous delivery for a period of time, e.g. intravenous delivery.

The compound may be an sRAGE polypeptide such as polypeptide analogs of sRAGE. Such analogs include fragments of sRAGE. Following the procedures of the published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of sRAGE polypeptide. Such products share at least one of the biological properties of sRAGE but may differ in others. As examples, products of the invention include those which are foreshortened by e.g., deletions; or those which are more stable to hydrolysis (and, therefore, may have more pronounced or longerlasting effects than naturally-occurring); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within sRAGE, which fragments may possess one property of sRAGE and not others. It is noteworthy that activity is not necessary for any one or more of the polypeptides of the invention to have therapeutic utility or utility in other contexts, such as in assays of sRAGE antagonism. Competitive antagonists may be quite useful in, for example, cases of overproduction of sRAGE.

Of applicability to polypeptide analogs of the invention are reports of the immunological property of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., Cell, 23, 309–310 (1981); Ross et al., Nature, 294, 654–658 (1981); Walter et al., Proc. Natl. Acad. Sci. USA, 78, 4882–4886 (1981); Wong et al., Proc. Natl. Sci. USA, 79, 5322–5326 (1982); Baron et al., Cell, 28, 395–404 (1982); Dressman et al., Nature, 295, 185–160 (1982); and Lerner, Scientific American, 248, 66–74 (1983). See also, Kaiser et al. [Science, 223, 249–255 (1984)] relating to biological and immunological properties of synthetic peptides which approximately share secondary structures of peptide hormones but may not share their primary structural conformation.

The compound of the present invention may be a peptidomimetic compound which may be at least partially unnatural. The peptidomimetic compound may be a small molecule mimic of a portion of the amino acid sequence of sRAGE. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include L-,D- or unnatural amino acids, alpha, alpha-disubstituted amino acids, N-alkyl amino acids, lactic acid (an isoelectronic analog of alanine). The peptide backbone of the compound may have at least one bond replaced with PSI—[CH═CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ϵ-amino caproic acid, 7-amino heptanoic acid, L-aspartic acid, L-glutamic acid, cysteine (acetamindomethyl), N-ϵ-Boc-N-α-CBZ-L-lysine, N-ϵ-Boc-N-α-Fmoc-L-lysine, L-methionine sulfone, L-norleucine, L-norvaline, N-ϵ-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

In another embodiment, the compound may be soluble RAGE (sRAGE) or a fragment thereof. Soluble RAGE is not located on the cell surface and is not associated with a cell membrane.

The subject may be a mammal or non-mammal. The subject may be a human. The subject may be a mouse, a rat, a cow, a monkey, a horse, a pig, or a dog. The subject may be a diabetic subject.

The administration of the compound may be intralesional, intraperitoneal, intramuscular or intravenous injection; infusion; liposome-mediated delivery; topical, nasal, oral, anal, ocular or otic delivery. The administration may be constant for a certain period of time or periodic and at specific intervals. The carrier may be a diluent, an aerosol, a topical carrier, an aqueous solution, a nonaqueous solution or a solid carrier.

In the practice of any of the methods of the invention or preparation of any of the pharmaceutical compositions a "therapeutically effective amount" is an amount which is capable of preventing interaction of EN-RAGE/RAGE in a subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of polypeptide compositions and compounds, together with suitable diluents, preservatives, solubilizers, emulsifiers, adjuvants and/or carriers. Such compositions may be liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts.

Such compositions will influence the physical state, solubility, stability, rate of in vivo release, and rate of in vivo clearance of the compound or composition. The choice of compositions will depend on the physical and chemical properties of the compound.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The polypeptide or composition of the present invention may be delivered in a microencapsulation device so as to reduce or prevent an host immune response against the polypeptide or against cells which may produce the polypeptide. The polypeptide or composition of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate group in proteins.

Pharmaceutical with Carriers

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient of the present invention (i.e., the compound identified by the screening method or composition thereof) can be administered orally in the form of a sterile solution or suspension on containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In another embodiment of the present invention, the subject may have diabetes. The subject may demonstrate complications associated with diabetes. Some examples of such complications include activation of endothelial and macrophage AGE receptors, altered lipoproteins, matrix, and basement membrane proteins; altered contractility and hormone responsiveness of vascular smooth muscle; altered endothelial cell permeability; sorbitol accumulation; neural myoinositol depletion or altered Na—K ATPase activity. Such complications are discussed in a recent publication by Porte and Schwartz, Diabetes Complications: Why is Glucose potentially Toxic?, Science, Vol. 272, pages 699–700.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

The present invention provides for a new proinflammatory cytokine-like molecule (EN-RAGE) (which has some sequence similarity to the family of calgranulin molecules). EN-RAGE is a protein located inside of inflammatory cells (such as neutrophils) and which may be released by such inflammatory cells. EN-RAGE has biological activity that may be responsible for the propagation and sustainment of an inflammatory response by interacting with cellular receptor RAGE.

Example 1

Interaction of EN-RAGE (Extracellular Novel Rage Binding Protein) with Receptor for AGE (RAGE) Perpetuates Inflammatory Responses: Suppression of Delayed-Type Hypersensitivity Reactions with Soluble Receptor for Age (sRAGE)

Expression of RAGE, the Receptor for Advanced Glycation Endproducts, is increased in the setting of inflammation. Here we report a new member of the calgranulin family of proinflammatory cytokines called EN-RAGE (or Extracellular Novel RAGE-binding protein), which interacts with RAGE on cells such as endothelial cells, to alter cellular properties in a manner consistent with perturbation. Administration of soluble RAGE (the extracellular ligand binding domain of RAGE; sRAGE) or anti-RAGE or anti-EN-RAGE F(ab')$_2$ fragments markedly attenuated inflammation in a model of delayed hypersensitivity. These data link RAGE to the inflammatory response and identify EN-RAGE and RAGE as novel targets for anti-inflammatory intervention. Soluble RAGE, furthermore, is thus a prototypic structure for the design of a new class of anti-inflammatory agents.

The Receptor for AGE (RAGE) is a member of the immunoglobulin superfamily of cell-surface molecules (1–2). Originally identified and characterized as a cellular receptor for glucose (aldose sugar)-modified proteins, or Advanced Glycation Endproducts (AGEs) (3–13), RAGE has subsequently been reported to interact with other ligands, in both settings of normal development and in Alzheimer's disease (14–16). In normal development, RAGE interacts with amphoterin, a polypeptide which mediates neurite outgrowth in cultured embryonic neurons. In those studies, either anti-RAGE F(ab')$_2$ or soluble RAGE (sRAGE) inhibited neurite outgrowth on amphoterin-coated matrices, but not on matrices coated with other substrates such as laminin or poly-l-lysine (3). In later studies, RAGE was identified as a receptor on neurons and microglia for amyloid-β-peptide, a polypeptide linked to the pathogenesis of neuronal toxicity and death in Alzheimer's disease.

In unpublished observations from our laboratory, we identified that increased RAGE expression was noted in the vascular and inflammatory cells of inflammatory lesions, such as in the kidney tissue from patients with active lupus nephritis (FIG. 1). We therefore hypothesized that RAGE might interact with alternative ligand(s) in that setting in order to, perhaps, participate in the inflammatory response.

Herein, the findings demonstrate that RAGE interacts with a molecule with close homology to calgranulin C. We have termed this molecule, EN-RAGE (Extracellular Novel RAGE binding protein) and show that EN-RAGE:RAGE interaction activates cells such as endothelial cells which are importantly involved in the inflammatory response. In a model of murine delayed hypersensitivity, administration of soluble RAGE (sRAGE), which contains the ligand interaction domain, inhibits the development of cellular activation and inflammation. These findings identify RAGE as a new target for anti-inflammatory intervention.

Materials and Methods

Isolation and Purification of EN-RAGE. Bovine lung acetone powder (SIGMA®) was subjected to solubilization in buffer containing tris (0.02M, pH 7.4); NaCl (0.15 M); octyl-β-glucoside (1%); and protease inhibitors (PMSF and aprotinin). After serial chromatography onto SP sepharose (Pharmacia LKB®), and affi-gel 10 resin (BIO-RAD®) to which had been adsorbed purified soluble human RAGE (prepared from a baculovirus expression system), RAGE-binding proteins were identified based on a screening assay employing immobilized column fraction (Nunc Maxisorp dishes) (NUNC®) and $^{125}$-I-labelled sRAGE as above. After elution with heparin-containing buffer (1 mg/ml), positive fractions were identified. RAGE-binding proteins were subjected to sequence analysis.

Cloning of EN-RAGE. The cDNA for EN-RAGE was cloned from a bovine lung library and placed into a baculovirus expression system. In this system, EN-RAGE, which lacks a leader sequence, was synthesized within Sf9 cells. EN-RAGE was then purified after solubilization of the cells in detergent-containing buffer, and sequential purification on hydroxylapatite and heparin-containing resins. The final product displayed a single band on Coomassie-stained SDS-PAGE gels and was devoid of endotoxin after chromatography onto Detoxi-gel columns (PIERCE®). Absence of detectable endotoxin was confirmed using *limulus amebocyte* assay (SIGMA®).

Sequence analysis. After SDS-PAGE identified an ≈12 kDa polypeptide with RAGE-binding activity, the gel band was eluted according to previously-published methods (17). The published method was modified by addition of a final wash of two aliquots (0.1 ml each) of guanidine (5.0M), urea (5.0M), trifluoroacetic acid (0.2%), acetonitrile (10%), and Zwittergent 3-08 (1.0%) (Calbiochem) to ensure that protein was completely washed from the filter. Amino-terminal sequence analysis was performed. Automated Edman degradation was carried out employing an HP-G1005A sequencer (Hewlett Packard Analytical Instruments). In order to obtain internal sequence, the gel bands were treated as above for elution, except that the extraction buffer contained half the usual amount of SDS (1). Endoproteinase Lys-C (1 μg) (Boehringer Mannheim) was added and the sample incubated overnight. The digest was then fractionated by microbore HPLC (Michrom Bioresources) on a 1 mm×50 mm PLRP—S column (Polymer Laboratories, Ltd.). The gradient utilized was 2% per minute from acetonitrile (5–75%) in trifluoroacetic acid (0.1%) and fractions were collected at 30 second intervals. Absorbance was monitored at 214 nm and fractions that corresponded to chromatographic peaks were then subjected to sequence analysis.

Endothelial cell activation. Human umbilical vein endothelial cells were isolated, characterized and maintained as previously described (18). Cells were cultured in serum-free RPMI 1640 without endothelial cell growth factor for 24 hrs and then stimulated with the indicated concentrations of EN-RAGE. Where indicated, cells were pretreated with rabbit anti-human RAGE IgG, nonimmune rabbit IgG; in certain cases, EN-RAGE was pretreated with the indicated concentration of soluble RAGE (sRAGE) for 2 hrs prior to stimulation with EN-RAGE. After eight hrs stimulation with EN-RAGE, cells were fixed with paraformaldehyde (2%) for 30 mins, washed twice with PBS, treated with PBS containing non-fat dry milk (5%) and BSA (2.5%) to block nonspecific binding sites on the cell surface. Cell surface ELISA employing anti-VCAM-1 IgG (Santa Cruz Biotechnologies, Santa Cruz, Calif.) was performed. Assessment of functional VCAM-1 activity was determined using $^{51}$Cr-labelled Molt-4 cells (ATCC) as previously described (10).

Delayed hypersensitivity model. A murine model of delayed hypersensitivity was established based on previously-published studies (19). Female CF-1 mice (Charles River laboratories), 6 weeks of age, were sensitized by subcutaneous injection over the left inguinal lymph node of an emulsion (0.1 ml) containing methylated BSA (mBSA; 25 mg/ml; SIGMA®), NaCl (0.9%), dextran (5–40×10$^6$ MW; 50 mg/ml; SIGMA®) and Freund's incomplete adjuvant (50%; ICN Biomedical). Three weeks later, the left plantar hind paw was injected subcutaneously with mBSA (0.4 mg/ml; 0.050 ml). Where indicated, mice were pretreated by intraperitoneal injection with sRAGE (indicated dose), mouse serum albumin (SIGMA®), immune or non-immune F(ab')$_2$ fragments (prepared using a kit from Pierce) 24 and 12 hrs prior to, and 6 and 12 hrs after local challenge with MBSA. 24 hrs after injection of foot pad with mBSA, clinical score of foot pad was performed; mice were then humanely sacrificed and feet fixed in formalin (10%) or frozen for further analysis. Histologic score was performed on sections of foot stained with hematoxylin and eosin (SIGMA®). The clinical score was defined as follows (scale; 1–5): 1=no inflammation and thus identical to untreated foot; 2=slight rubor and edema; 3=severe rubor and edema with wrinkling of the skin of the foot pad; 4=severe rubor and edema without wrinkling of the skin of the foot pad; and 5=severe rubor and edema resulting in spreading of the toes. The histologic score after hematoxylin and eosin staining was defined as follows (scale; 1–5): 1=no leukocytic infiltration with slight subcutaneous edema;

2=slight perivascular leukocytic infiltration with slight subcutaneous edema; 3=severe leukocytic infiltration without granulomata; and 4=severe leukocytic infiltration with granulomata.

Results

Identification of EN-RAGE. After a serial series of experiments designed to identify RAGE-binding proteins from bovine lung extract (from where RAGE was originally purified), an ≈12 kDa polypeptide was identified. Upon sequence analysis, this polypeptide was found to bear significant homology to members of the calgranulin C family of proteins (Table 1) (20–21). This class of proteins exist intracellularly within inflammatory cells. Upon release in inflamed loci, we postulated they might be able to, in turn, engage and activate other cells already recruited into the inflammatory response. Thus, this might represent an important means by which the inflammatory response might be propagated and sustained, thereby increasing the probability of cellular injury.

Figure 2:
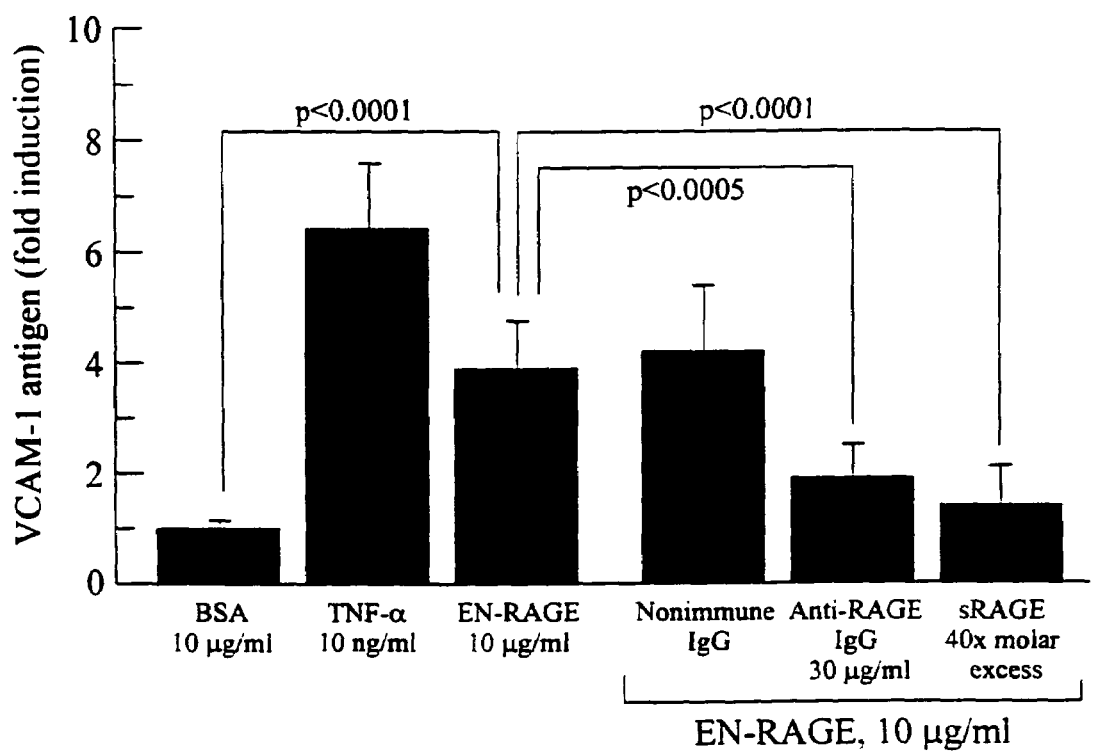
FIG. 2. Incubation of HUVECs with EN-RAGE results in increased cell surface VCAM-1. Human umbilical vein endothelial cells were cultured in serum-free RPMI 1640 without endothelial cell growth factor for 24 hrs and then stimulated with EN-RAGE or bovine serum albumin (BSA); both 10 µg/ml. Where indicated, cells were pretreated with rabbit anti-human RAGE IgG, nonimmune rabbit IgG; in certain cases, EN-RAGE was pretreated with the indicated concentration of soluble RAGE (sRAGE) for 2 hrs prior to stimulation with EN-RAGE. After eight hrs stimulation with EN-RAGE, cells were fixed as described above. Cell surface ELISA employing anti-VCAM-1 IgG was performed. Statistical considerations are shown in the figure.

EN-RAGE activates endothelial cells in a RAGE-dependent manner. To test this hypothesis, EN-RAGE was purified as described above and incubated with endothelial cells. Incubation of EN-RAGE with HUVEC resulted in increased cell surface Vascular Cell Adhesion Molecule-1 (VCAM-1) in a RAGE-dependent manner (FIG. 2). These data suggested that in an inflammatory focus, interaction of EN-RAGE with EC RAGE might represent a means by which to further propagate an inflammatory response. Consistent with increased VCAM-1 antigen on the surface of EN-RAGE-treated ECs, increased binding for Molt-4 cells (which bear the ligand for VCAM-1, VLA-4), ensued (FIG. 3). While incubation with either BSA or non-immune IgG did not affect the ability of EN-RAGE to activate EC VCAM-1, incubation with either sRAGE or anti-RAGE F(ab')$_2$ significantly attenuated the ability of EN-RAGE to increase Molt-4 binding to treated HUVEC.

We sought to test these hypotheses in in vivo models. We demonstrated that in diabetic mice, in which the ligand for RAGE is likely to be, at least in part, products of glycation/oxidation of proteins/lipids, the Advanced Glycation Endproducts, or AGEs, administration of the soluble, ligand-binding portion of RAGE (soluble or sRAGE), suppressed accelerated atherosclerosis in diabetic apolipoprotein E null mice (12) and improved wound healing in genetically-diabetic db+/db+mice (22). Thus, the biologic effects of EN-RAGE in highly-inflammatory foci, such as those characterized by models of granulomatous inflammatory lesions (delayed hypersensitivity), could be suppressed in the presence of sRAGE.

To test this, we studied a model of delayed hypersensitivity (DH) in which mice were first sensitized by injection of methylated BSA (mBSA; which does not bind RAGE) over the inguinal lymph nodes of female CF-1 mice. Three weeks after sensitization, mice were challenged with mBSA by injection into the hind foot pad. An inflammation score was designed on a scale of 1–9 which included both clinical score (1–4) and histologic score (1–5) as indicated in FIG. 4.

Consistent with our hypothesis, administration of sRAGE suppressed inflammation upon injection of mBSA into the foot pad of mice previously-sensitized with mBSA over the lymph nodes, in a dose-dependent manner (FIG. 4). At a dose of 100 μg sRAGE, inflammation was markedly suppressed ($p<0.01$). In contrast, administration of mouse serum albumin, had no effect on the appearance of the inflammatory lesion (FIG. 4). Consistent with an important role for EN-RAGE and RAGE in the development of inflammation in this model, treatment of the mice with either anti-EN-RAGE F(ab')$_2$ or anti-RAGE F(ab')$_2$ considerably suppressed inflammation ($p<0.05$ in each case compared with treatment with nonimmune F(ab')$_2$. When mice were treated with both anti-EN-RAGE and anti-RAGE F(ab')$_2$, even further suppression of the inflammatory response eventuated ($p<0.05$ compared with treatment with nonimmune F(ab')$_2$ (FIG. 4).

DISCUSSION

The inflammation phenotype observed in delayed-type hypersensitivity reactions certainly represent the culmination of a complex interplay and contribution of multiple cell types and their cellular mediators. In the development of inflammation, an important source of the stimuli may be from the inflammatory cells themselves. Upon initial recruitment into an inflammatory locus, cells such as neutrophils and macrophages may release mediators such as those of the calgranulin family, including EN-RAGE, and propagate and sustain the inflammatory response. Such mediators, such as EN-RAGE, likely require cellular receptors to initiate events that will culminate in altered gene expression.

Our data strongly suggest that EN-RAGE-RAGE interaction is an important factor in these processes. Nearly complete suppression of inflammation was noted in the presence of sRAGE, in a dose-dependent manner. Based upon our studies, sRAGE may act as a decoy in this setting to bind EN-RAGE prior to its ability to engage RAGE-bearing cells implicated in the inflammatory response. Furthermore, in the presence of anti-RAGE/anti-EN-RAGE or anti-RAGE+anti-EN-RAGE F(ab')$_2$, substantial suppression of inflammation was observed, further indicating a role of these factors in the modulation of the inflammatory response.

It is important to note, of course, that alternate mechanisms underlying the beneficial effects of sRAGE may be operative in these settings. However, the studies noted above employing the indicated F(ab')$_2$ fragments, strongly implicate EN-RAGE and RAGE in the evolution of the inflammatory response in this setting.

In conclusion, the studies presented herein implicate RAGE centrally in the inflammatory response and identify soluble RAGE as a prototypic structure for the development of novel, anti-inflammatory agents.

Note: FIG. 5 shows the nucleic acid sequence (cDNA sequence) of bovine EN-RAGE.

TABLE 1

Sequence analysis of EN-RAGE and comparison with related proteins.

|  | 10 20 30 |
|---|---|
| EN-RAGE (SEQ ID NO:2) | TKLEDHLEGIINIGHQYSVRVGHFDTLNKY – |

TABLE 1-continued

Sequence analysis of EN-RAGE and comparison
with related proteins.

| N-TERM Endo Lys C (SEQ ID NO.5) | |
|---|---|
| B-COAg (SEQ ID NO.3) | TKLEDHLEGIINIFHQYSVRVGHFDTLNKR |
| B-CAAF1 (SEQ ID NO.4) | TKLEDHLEGIINIFHQYSVRVGHFDTLNKR |
| | 31       40       50       60 |
| EN-RAGE N-TERM Endo Lys C | ELKQLGTKELPKTLQNXKDQ |
| B-COAg | ELKQLITKELPKTLQNTKDQPTIDKIFQDL |
| B-CAAF1 | ELKQLITKELPKTLQNTKDQPTIDKIFQDL |
| | 61       70       80       90 |
| EN-RAGE N-TERM Endo Lys C | DGAVSFEEFVVLVSRVLK |
| B-COAg | DADKDGAVSFEEFVVLVSRVLKTAHIDIHK |
| B-CAAF1 | DADKDGAVSFEEFVVLVSRVLKTAHIDIHK |

Example 2

EN-RAGE (Extracellular Novel-RAGE Binding Protein) Activated Endothelial Cells to Mediate Inflammatory Responses The expression of Receptor for AGE (RAGE) is enhanced in inflammatory settings such as atherosclerosis and autoimmune vasculitities. We hypothesized that Receptor for AGE (RAGE) might interact with alternative ligands beyond Advanced Glycation Endproducts (AGEs) in such settings. We isolated and purified an ≈12 kDa polypeptide from extract of bovine lung which bore homology to the calgranulin family of proinflammatory mediators. This polypeptide, called EN-RAGE, binds immobilized RAGE and endothelial (EC)/macrophage (MP) RAGE in culture wells with Kd≈75 nM, processes blocked in the presence of anti-RAGE IgG or soluble (sRAGE; the extracellular two-thirds of RAGE). In vitro, exposure of cultured ECs to EN-RAGE increased activation of NF-kB, expression of cell-surface VCAM-1 (4.3-fold compared to treatment with bovine serum albumin BSA), and adhesion of Molt-4 cells (which bear VLA-4, the counter-ligand for VCAM-1)(7-fold compared with BSA), all in a manner inhibited in the presence of anti-RAGE IgG or sRAGE. Exposure of macrophages to EN-RAGE resulted in increased chemotaxis in a RAGE-dependent manner. To test these concepts in vivo, we utilized a model of delayed hypersensitivity in mice in which footpad injections of methylated BSA (mBSA) induce localized inflammation. Pre-treatment (intraperitoneal; IP) with sRAGE prevented mBSA-mediated inflammation in a dose-dependent manner. At 100 μg IP sRAGE, the mBSA-treated foot manifested no inflammation and markedly diminished activation of NF-kB compared with mice treated with vehicle, mouse serum albumin (MSA); further, elaboration of TNF-alpha into the serum was completely prevented. Partial anti-inflammatory responses were observed upon treatment of the mice with either anti-RAGE or anti-EN-RAGE F(ab')2. Nonimmune F(ab')2 was without effect. Taken together, these findings indicate that ligands alternative to AGEs such as EN-RAGE activate ECs and MPs, thereby linking RAGE to the generalized inflammatory response.

Example 3 sRAGE Results in Diminished Mortality After Endotoxemia: A Potential Treatment for Septic Shock The use of sRAGE or compounds which are capable of inhibiting the interaction of EN-RAGE and RAGE could be useful agents for the treatment of septic shock or sepsis in subjects. It has been shown that a subject given lethal doses of LPS has reduced mortality when the LPS is given in the presence of sRAGE.

sRAGE and Endotoxemia

Soluble Receptor for AGE (sRAGE) has been shown to prevent inflammation in a model of delayed-type hypersensitivity. Unlike certain anti-inflammatory-type agents, it was believed that sRAGE might exert beneficial effects when administered in the setting of endotoxemia, a prototypic result of, for example, profound gram negative bacteremia. When uniformly lethal doses of LPS were administered to Balb/C mice (≈750 μg), administration of sRAGE (pre or post LPS injection) prevented death in ≈50% of the mice in pilot studies.

These data underscore the proposition that the potent anti-inflammatory effects of sRAGE are not associated with an untoward inclination toward morbidity/mortality due to the presence of septicemia/endotoxemia. SRAGE, therefore, may be a selective anti-inflammatory agent with selective protective effects against maladaptive inflammatory responses.

REFERENCES

1. Schmidt, A. M., Vianna, M., Gerlach, M., Brett, J., Ryan, J., Kao, J., Esposito, C., Hegarty, H., Hurley, W., Clauss, M., Wang, F., Pan, Y. C., Tsang, T. C., and Stern, D. Isolation and characterization of binding proteins for advanced glycosylation endproducts from lung tissue which are present on the endothelial cell surface. J. Biol. Chem. 267:14987–14997, 1992.
2. Neeper, M., Schmidt, A. M., Brett, J., Yan, S. D., Wang, F., Pan, Y. C., Elliston. K., Stern, D., and Shaw, A. Cloning and expression of RAGE: a cell surface receptor 3. Schmidt, A-M, Hori, 0, Brett, J, Yan, S-D, Wautier, J-L, and Stern D. Cellular receptors for advanced glycation end products. Arterioscler. Thromb. 14:1521–1528, 1994.
4. Schmidt, A. M., S D Yan, and D. Stern. The Dark Side of Glucose (News and Views). Nature Medicine 1:1002–1004, 1995.
5. Yan, S-D, Schmidt, A-M, Anderson, G, Zhang, J, Brett, J, Zou, Y-S, Pinsky, D, and Stern, D. Enhanced cellular oxidant stress by the interaction of advanced glycation endproducts with their receptors/binding proteins. J. Biol. Chem. 269:9889–9897, 1994.
6. Schmidt, A-M, Yan, S-D, Brett, J, Mora, R, Nowygrod, R, and Stern D. Regulation of mononuclear phagocyte migration by cell surface binding proteins for advanced glycosylation endproducts. J. Clin. Invest. 92:2155–2168, 1993.
7. Wautier, J L, Chappey, O, Wautier, M P, Hori, O, Stern, D, and Schmidt A M. Receptor-mediated endothelial dysfunction in diabetic vasculopathy: sRAGE blocks hyperpermeability. J. Clin. Invest. 97:238–243, 1996.
8. Miyata, T., Hori, 0, Zhang, J H, Yan, S D, Ferran, L, Iida, Y, and Schmidt, A M. The Receptor for Advanced Glycation Endproducts (RAGE) mediates the interaction of AGE-b$^2$-Microglobulin with human mononuclear phagocytes via an oxidant-sensitive pathway: implications for the pathogenesis of dialysis-related amyloidosis. J. Clin. Invest. 98:1088–1094, 1996.
9. Schmidt, A-M, Hasu, M, Popov, D, Zhang, J-H, Chen, J, Yan, S-D, Brett, J, Cao, R, Kuwabara, K, Gabriela, C, Simionescu, N, Simionescu, M, and Stern D. Receptor for advanced glycation endproducts (AGEs) has a central role in vessel wall interactions and gene activation in response to circulating AGE proteins. PNAS(USA) 91:8807–8811, 1994.
10. Schmidt, A M, Hori, O, Chen, J, Brett, J, and Stern, D. AGE interaction with their endothelial receptor induce expression of VCAM-1: a potential mechanism for the accelerated vasculopathy of diabetes. J. Clin. Invest. 96:1395–1403, 1995.
11. Lander, H. L., Tauras, J. M., Ogiste, J. S., Moss, R. A., and A. M. Schmidt. Activation of the Receptor for Advanced Glycation Endproducts triggers a MAP Kinase pathway regulated by oxidant stress. J. Biol. Chem. 272:17810–17814, 1997.
12. Park, L., Raman, K. G., Lee, K. J., Yan, L., Ferran, L. J., Chow, W. S., Stern, D., and Schmidt, A. M. Suppression of accelerated diabetic atherosclerosis by soluble Receptor for AGE (sRAGE). Nature Medicine 4:1025–1031, 1998.
13. Wautier J L, Chappey 0, Wautier M P, Boval B, Stern D and A M Schmidt. Interaction of diabetic erythrocytes bearing advanced glycation endproducts with the endothelial receptor RAGE induces generation of reactive oxygen intermediates and cellular dysfunction. Circ. 94 (8):#4139, 1996.
14. Hori, O., J. Brett, T. Slattery, R. Cao, J. Zhang, J. Chen, M. Nagashima, D. Nitecki, J. Morser, D. Stern, A. M. Schmidt. The Receptor for Advanced Glycation Endproducts (RAGE) is a cellular binding site for amphoterin: mediation of neurite outgrowth and co-expression of RAGE and amphoterin in the developing nervous system. J. Biol. Chem. 270:25752–25761, 1995.
15. Yan, S D, X. Chen, J. Fu, M. Chen, H. Zhu, A. Roher, T. Slattery, M. Nagashima, J. Morser, A. Migheli, P. Nawroth, G. Godman, D. Stern, and A. M. Schmidt. RAGE and amyloid-b peptide neurotoxicity in Alzheimer's disease. Nature 382:685–691, 1996.
16. Yan, S-D., Zhu, H., Fu, J., Yan, S—F., Roher, A., Tourtellotte, W., Rajavashisth, T., Chen, X., Stern, D. and Schmidt, A-M. Amyloid-beta peptide-RAGE interaction elicits neuronal expression of M-CSF: a proinflammatory pathway in Alzheimer's disease. Proc. Natl. Acad. Sci. 94:5296–5301, 1997.
17. Slattery, T. K. and Harkins, R. N. Techniques in protein chemistry IV, ed. Angeletti, R. H., Academic Press, San Diego, Calif., 1992.
18. Jaffe, E., Nachman, R., Becker, C., and Minick, R. Culture of human endothelial cells derived from umbilical veins. Identification by morphologic and immunologic criteria. J. Clin. Invest. 52:2745–2756, 1973.
19. Dunn, C. J., Galinet, L. A., Wu, H., Nugent, R. A., Schlachter, S. T., Staite, N. D., Aspar, D. G., Elliott, G. A., Essani, N. A., Rohloff, N. A., and Smith, R. J. Demonstration of novel anti-arthritic and anti-inflammatory effects of diphosphonates. J. Pharmacology and Experimental Therapeutics 266: 1691–1698, 1993.
20. Wicki, R., Marenholz, I., Mischke, D., Schafer, B. W., and Heizmann, C. W. Characterization of the human S100A12 (calgranulin C, p6, CAAF1, CGRP) gene, a new member of the S100 gene cluster on chromosome 1q21. Cell Calcium 20:459–464, 1996.
21. Dell'Angelica, E. C., Schleicher, C. H., and Santome, J. A. Primary structure and binding properties of calgranulin C, a novel S100-like calcium-binding protein from pig granulocytes. J. Biol. Chem. 269:28929–28936, 1994.
22. Wu J, Rogers L, Stern D, Schmidt A M and Chiu D T W. The soluble receptor for Advanced Glycation Endproducts (sRAGE) ameliorates impaired wound healing in diabetic mice. Plastic Surgery Research Council, Abstract #77, p. 43, 1997.

What is claimed is:

1. A method for inhibiting inflammation in a subject which comprises administering to the subject a compound selected from the group consisting of (i) an anti-EN-RAGE antibody, (ii) an EN-RAGE-binding fragment of an anti-EN-RAGE antibody, (iii) the V-domain of soluble RAGE polypeptide or (iv) an EN-RAGE-binding fragment of the V-domain of soluble RAGE polypeptide, thereby inhibiting inflammation in the subject.

2. The method of claim 1, wherein the inflammation is associated with delayed hypersensitivity, accelerated atherosclerosis, or lupus nephritis.

3. The method of claim 1, wherein the subject is a human, a primate, a mouse, a rat or a dog.

4. The method of claim 1, wherein the administration comprises intralesional, intraperitoneal, intramuscular or intravenous injection; infusion; liposome-mediated delivery; or topical, intrathecal, per rectum, gingival pocket, intrabronchial, nasal, oral, ocular or otic delivery.

5. The method of claim 1, wherein the compound is administered hourly, daily, weekly, monthly or annually.

6. The method of claim 1, wherein the effective amount of the compound comprises from about 0.000001 mg/kg body weight to about 100 mg/kg body weight.

7. The method of claim 1, wherein the subject is suffering from systemic lupus erythematosus, inflammatory lupus nephritis, septic shock or endotoxemia.

8. The method of claim 1, further comprising administering to the subject a pharmaceutically acceptable carrier during the administration of the compound.

9. The method of claim 8, wherein the carrier comprises a diluent.

10. The method of claim 8, wherein the carrier comprises a virus, a liposome, a microencapsule, a polymer encapsulated cell or a retroviral vector.

11. The method of claim 8, wherein the carrier is an aerosol, intravenous, oral or topical carrier.

12. The method of claim 8, wherein the compound is administered from a time release implant.

13. The method of claim 1, wherein the subject is suffering from an autoimmune or inflammatory disorder in which the recruitment of EN-RAGE-containing inflammatory cells occurs.

14. The method of claim 1, wherein the subject is suffering from a bacterial-associated or other pathogen-associated infection.

15. The method of claim 1, wherein the antibody is a monoclonal antibody or a polyclonal antibody.

16. The method of claim 1, wherein the antibody is a chimeric antibody, a humanized antibody or a primatized antibody.

17. The method of claim 1, wherein the compound is an anti-EN-RAGE antibody.

18. The method of claim 1, wherein the compound is an EN-RAGE-binding fragment of an anti-EN-RAGE antibody.

19. The method of claim 1, wherein the compound is the V-domain of soluble RAGE polypeptide.

20. The method of claim 1, wherein the compound is an EN-RAGE-binding fragment of the V-domain of soluble RAGE polypeptide.

* * * * *